(12) United States Patent
Cook et al.

(10) Patent No.: US 9,980,803 B2
(45) Date of Patent: May 29, 2018

(54) MEDICAL DEVICE RETRIEVAL SYSTEM AND METHOD

(71) Applicant: Cook Medical Technologies LLC, Bloomington, IN (US)

(72) Inventors: Leslie Cook, Indianapolis, IN (US); Nathan Kemper, Crestline, OH (US); Don Patterson, Bloomington, IN (US); John Tyler Strader, Elizabethtown, KY (US); Thomas Adam Treloar, Loveland, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 112 days.

(21) Appl. No.: 14/638,341

(22) Filed: Mar. 4, 2015

(65) Prior Publication Data

US 2015/0250578 A1   Sep. 10, 2015

Related U.S. Application Data

(60) Provisional application No. 61/948,233, filed on Mar. 5, 2014.

(51) Int. Cl.
*A61F 2/01* (2006.01)
*A61B 17/221* (2006.01)
*A61B 17/22* (2006.01)

(52) U.S. Cl.
CPC .............. *A61F 2/01* (2013.01); *A61B 17/221* (2013.01); *A61B 2017/2215* (2013.01); *A61B 2017/22035* (2013.01); *A61F 2002/011* (2013.01); *A61F 2002/016* (2013.01)

(58) Field of Classification Search
CPC .................. A61F 2/01; A61F 2002/011; A61F 2002/016; A61F 2/013; A61B 17/221; A61B 2017/22035; A61B 2017/2215
USPC ......................................................... 606/200
See application file for complete search history.

(56) References Cited

U.S. PATENT DOCUMENTS

| 5,549,626 | A | | 8/1996 | Miller et al. |
| 5,662,671 | A | * | 9/1997 | Barbut ........... A61B 17/320783 |
| | | | | 604/104 |
| 6,676,692 | B2 | | 1/2004 | Rabkin et al. |
| 6,699,260 | B2 | | 3/2004 | Dubrul et al. |

(Continued)

FOREIGN PATENT DOCUMENTS

| WO | 2012/011097 A1 | 1/2012 |
| WO | 2012/049652 A1 | 4/2012 |

*Primary Examiner* — Christopher L Templeton
*Assistant Examiner* — George J Ulsh
(74) *Attorney, Agent, or Firm* — Brinks Gilson & Lione

(57) ABSTRACT

A retrieval system for a medical device includes an access sheath, a clot catch with an attached mesh, and a filter catch having an attached retrieval member. The filter catch is translatable within clot catch, and the clot catch is translatable within the access sheath. The mesh is expandable into engagement with a body vessel during retrieval of the medical device. The mesh captures emboli that are dislodged during retrieval of the device. The device is captured by the clot catch during retrieval, and the clot catch is subsequently captured by the access sheath. The system can further include an inner sheath translatable within the clot catch, with the inner sheath capturing the medical device and the clot catch capturing the inner sheath.

17 Claims, 7 Drawing Sheets

(56) References Cited

U.S. PATENT DOCUMENTS

| | | | |
|---|---|---|---|
| 6,896,690 B1 * | 5/2005 | Lambrecht | A61F 2/2427 604/96.01 |
| 7,232,452 B2 * | 6/2007 | Adams | A61B 17/12136 606/200 |
| 7,815,676 B2 | 10/2010 | Greenberg | |
| 8,025,668 B2 | 9/2011 | McCartney | |
| 2005/0015112 A1 * | 1/2005 | Cohn | A61F 2/2412 606/200 |
| 2006/0155305 A1 | 7/2006 | Freudenthal et al. | |
| 2007/0088382 A1 | 4/2007 | Bei et al. | |
| 2007/0088383 A1 | 4/2007 | Pal et al. | |
| 2007/0225750 A1 * | 9/2007 | Ren | A61F 2/013 606/200 |
| 2009/0182370 A1 | 7/2009 | Volobuyev et al. | |
| 2009/0299393 A1 | 12/2009 | Martin et al. | |
| 2011/0208134 A1 | 8/2011 | Castella et al. | |
| 2011/0288529 A1 | 11/2011 | Fulton | |
| 2012/0179181 A1 | 7/2012 | Straub et al. | |

* cited by examiner

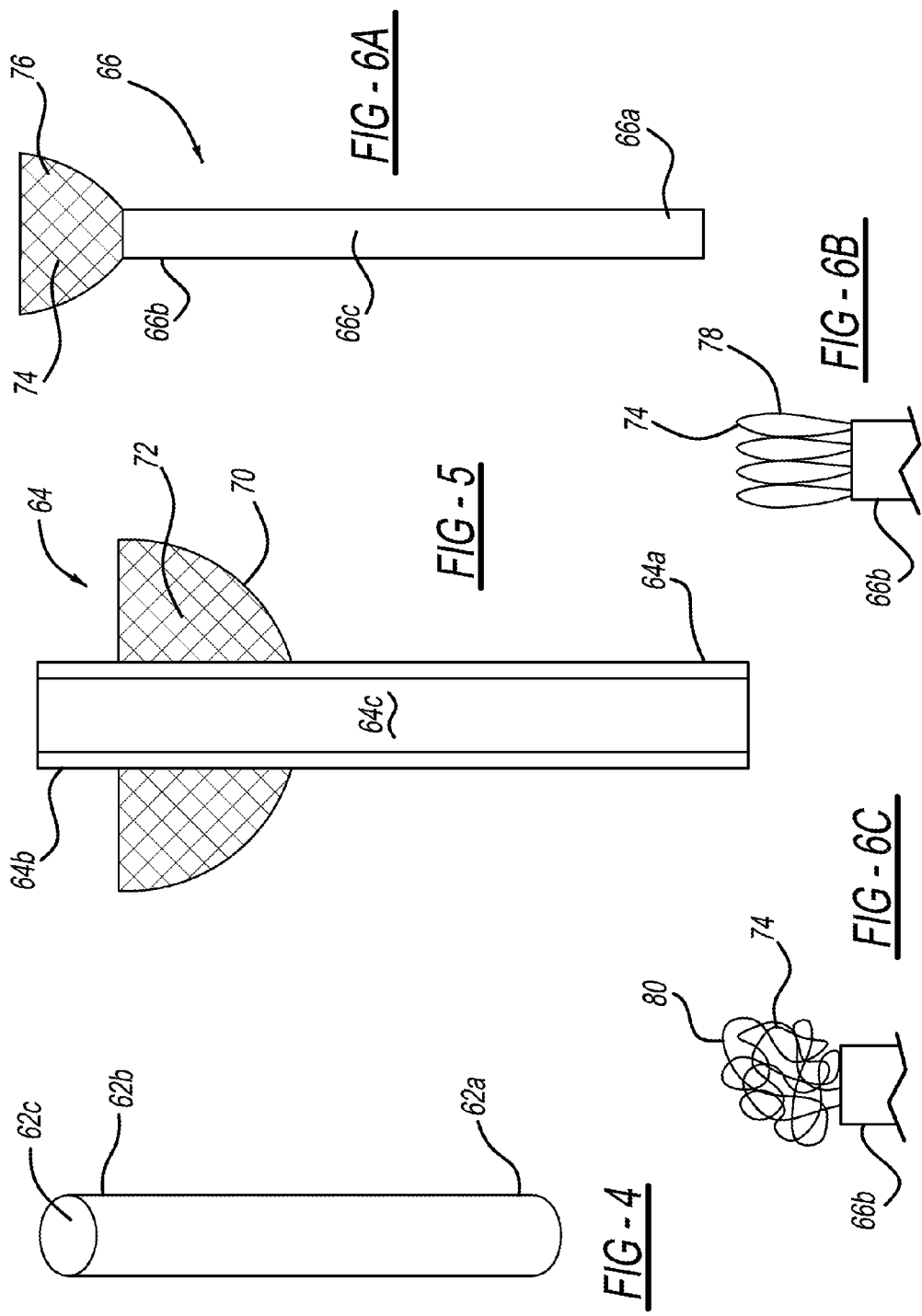

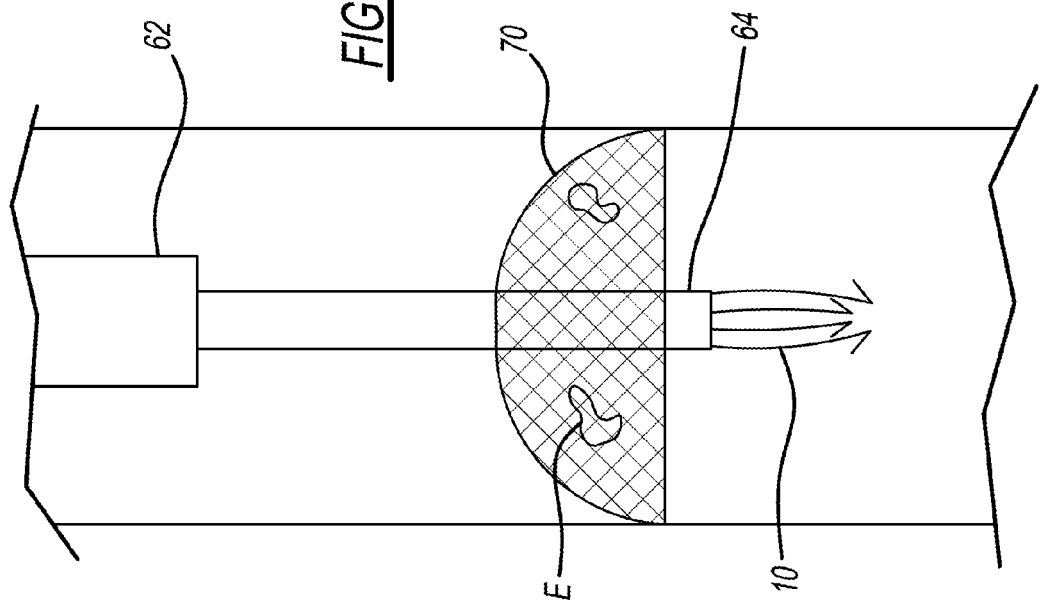
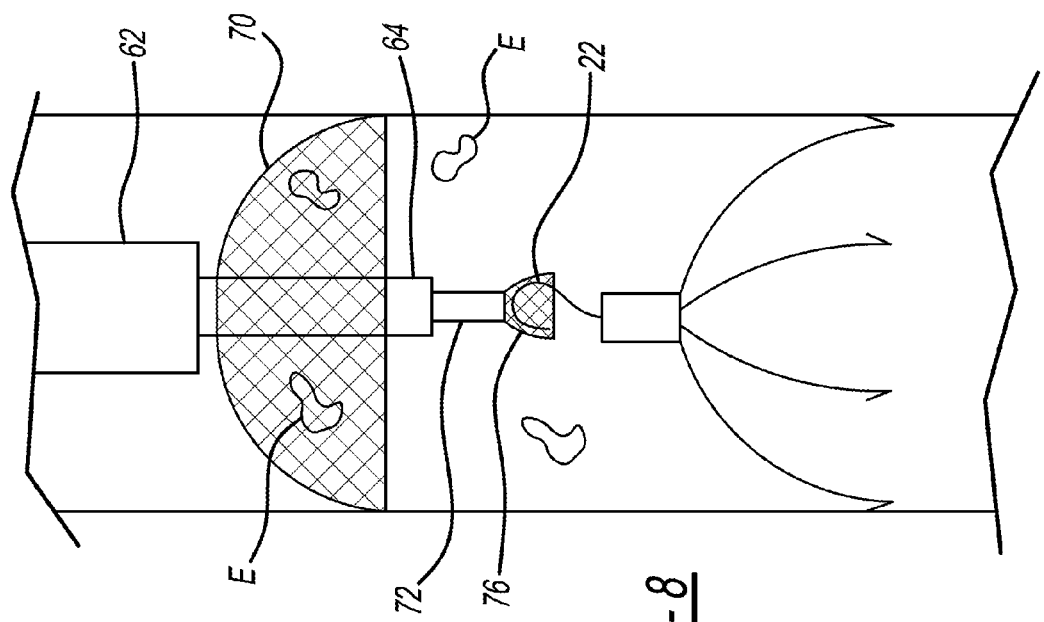

MEDICAL DEVICE RETRIEVAL SYSTEM AND METHOD

CROSS REFERENCE TO RELATED APPLICATIONS

This application claims the benefit of U.S. Provisional Patent Application No. 61/948,233, filed on Mar. 5, 2014, the entire contents of which is hereby incorporated by reference.

FIELD OF THE INVENTION

The present invention relates to medical devices. More particularly, the invention relates to a retrieval device for retrieving a removable vena cava clot filter from the vena cava of a patient.

BACKGROUND OF THE INVENTION

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

After deployment of a generally conical filter in a patient, the filter will generally become anchored to the wall of the vena cava or other body lumen in which it was delivered. Proliferating intimal cells begin to accumulate around the filter parts which contact the wall of the vessel. After a length of time, such ingrowth prevents removal of the filter without risk of trauma so that the filter is permanently left in the patient.

Moreover, conventional filters commonly become off-centered or tilted with respect to the hub of the filter and the longitudinal axis of the vessel in which it has been inserted. As a result, the filter including the hub and the retrieval hook engage the vessel wall along their lengths and potentially become endothelialized therein. As a result, the filter becomes a permanent implant in a shorter time period than otherwise.

After filtering is complete, or after filtering is no longer desirable or effective, it may be desirable to retrieve the filter from the vena cava. If the filter has tilted or has otherwise become ingrown into the tissue, retrieval according to known methods may become more difficult. Moreover, during retrieval, emboli that have become trapped in the filter may become dislodged and can re-enter the bloodstream, which is undesirable.

Accordingly, improvements may be made related to the retrieval of vena cava filters.

SUMMARY

One embodiment of the present invention generally provides a system for retrieving a medical device from within a body lumen, the system comprising: an access sheath having proximal and distal ends, corresponding proximal and distal openings, and a lumen extending therebetween and defining a longitudinal axis; an intermediate tube or clot catch having proximal and distal ends, corresponding proximal and distal openings, and a lumen extending therebetween, wherein the intermediate tube is disposed at least partially within the access sheath lumen and movable longitudinally relative to the access sheath; a first mesh member coupled to the intermediate tube and being biased radially outward to define a concave shape with a concavity facing the distal direction; and a retrieval device having an elongate shape and having proximal and distal ends, and a retrieval member coupled thereto, wherein the retrieval device is disposed at least partially within the lumen of the intermediate tube and moveable longitudinally relative to the intermediate tube; wherein the system includes a delivery configuration with the retrieval member and the distal end of the intermediate tube being disposed proximally of the distal opening of the access sheath; and wherein the system includes a retrieval configuration with the retrieval member disposed distally of the distal opening of the intermediate tube, the first mesh member disposed distally of the distal opening of the access tube and expanded radially outward to define the concave shape.

In an additional or alternative embodiment, the system can further include an inner sheath having proximal and distal ends, corresponding proximal and distal openings, and a lumen extending therebetween, wherein the inner sheath is disposed within the intermediate sheath, and the retrieval device is disposed within the inner sheath.

In an additional or alternative embodiment, a method for retrieving a medical device from a body vessel is provided, the method comprising: delivering a retrieval system in a delivery configuration toward a medical device located within a body vessel, the retrieval system comprising: an access sheath having proximal and distal ends and defining a lumen extending therebetween; a clot catch having proximal and distal ends and defining a lumen extending therebetween, the clot catch being housed within the lumen of the access sheath; an expandable mesh attached to the clot catch and being housed within the lumen of the access sheath; a filter catch having proximal and distal ends and being housed within the lumen of the clot catch; and a retrieval member attached to an end of the filter catch. The method further comprises extending the clot catch distally from the access sheath; exposing the expandable mesh from the access sheath; expanding the expandable mesh into engagement with a wall of the body vessel; extending the filter catch and retrieval member distally from the clot catch; capturing a portion of a medical device with the retrieval member; capturing at least a portion of the medical device within the clot catch; capturing the clot catch and the expandable mesh within the access sheath; and retracting the system proximally.

Further details and benefits of the present invention become apparent from the following description of drawings illustrating preferred embodiment of the invention. The drawings are presented herein solely for illustrative purposes and are not intended to limit the scope of the present invention.

BRIEF DESCRIPTION OF THE DRAWINGS

FIG. 4 illustrates an access sheath of the system;

FIG. 5 illustrates an intermediate tube or clot catch of the system having a radially expandable mesh;

FIG. 6A illustrates a filter catch of the system having a retrieval member in the form of a second mesh;

FIG. 6B illustrates an alternative retrieval member in the form of a plurality of loops;

FIG. 6C illustrates an alternative retrieval member in the form of a flexible member having a random tortuous path;

FIGS. 8-10 illustrate a method for retrieving the filter using the system of FIG. 3.

DETAILED DESCRIPTION OF THE DRAWINGS

Figure 1:
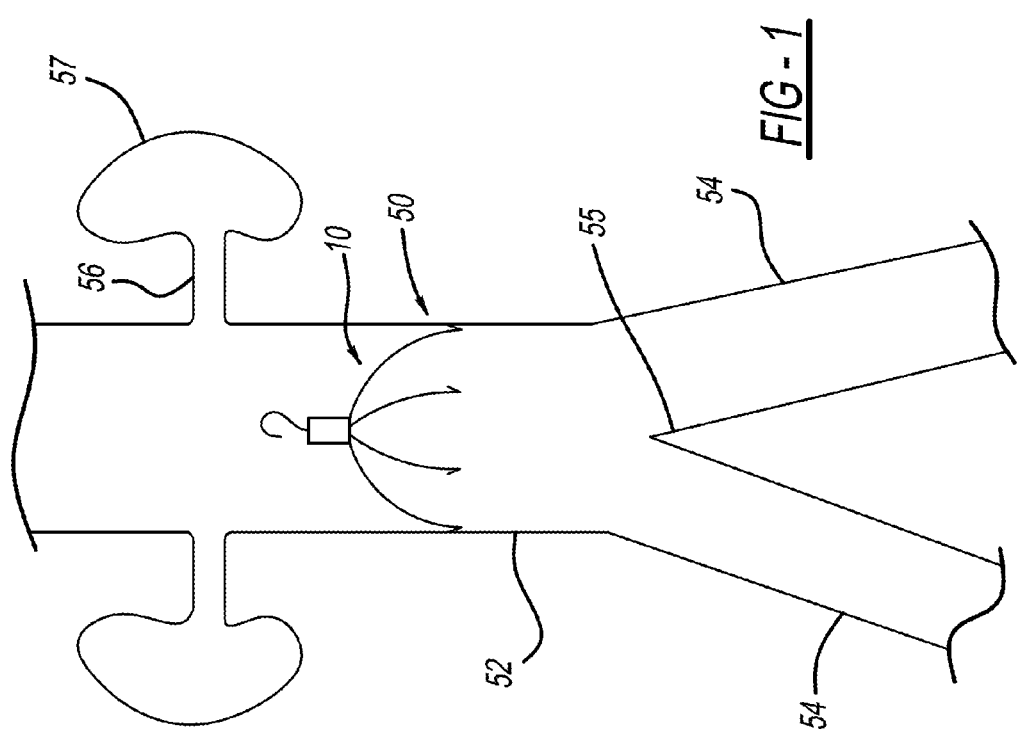
FIG. 1 is a schematic view of an inferior vena cava and a medical device or vena cava filter deployed therein.

In accordance with one embodiment of the present invention, FIG. 1 illustrates a vena cava filter 10 implanted in the vena cava 50 for the purpose of lysing or capturing thrombi carried by the blood flowing through the iliac veins 54 toward the heart and into the pulmonary arteries. As shown, the iliac veins merge at juncture 55 into the vena cava 50. The renal veins 56 from the kidneys 57 join the vena cava 50 downstream of juncture 58. The portion of the vena cava 50, between the juncture 55 and the renal veins 56, defines the inferior vena cava 52 in which the vena cava filter 10 has been percutaneously deployed through one of the femoral veins or through other known deployment methods. Preferably, the vena cava filter 10 has a length smaller than the length of the inferior vena cava 52. If the lower part of the filter extends into the iliac veins, filtering effectiveness will be compromised and if the filter wires cross over the origin of the renal veins the filter wires might interfere with the flow of blood from the kidneys.

Figure 2:
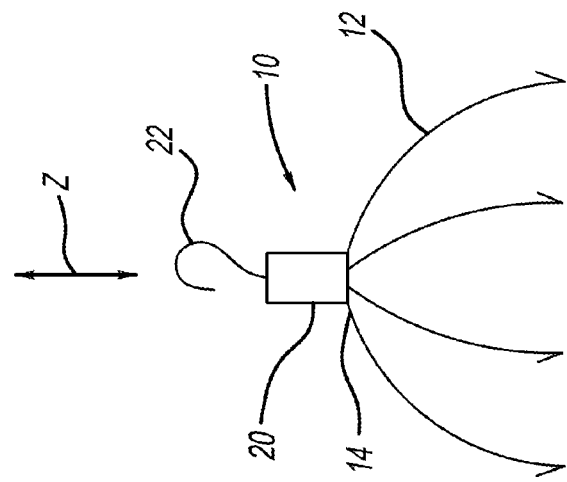
FIG. 2 illustrates the filter.

This embodiment of the present invention will be further discussed with reference to FIGS. 1-14, in which a system 60 or 160 for retrieving the filter 10 from the vena cava is shown. FIG. 2 illustrates the filter 10 in an expanded state, which is the state of the filter 10 after being delivered and deployed within the vena cava in a manner known in the art. The filter 10 includes a plurality of filter struts 12 each having first ends 14 that emanate from a hub 20. While four struts 12 are illustrated, it will be appreciated that other quantities of struts can also be used to suit the needs of the user. The hub 20 attaches by crimping the first ends 14 of the struts 12 together in a compact bundle along a central or longitudinal axis Z of the filter 10. The hub 20 has a minimal diameter for the size of wire used to form the struts. The filter 10 can also include, and preferably includes, a retrieval hook 22 attached to the hub 20. The hook 22 can have a traditional hook shape, or could have another form configured for attachment to a retrieval device.

Preferably, the filter struts 12 are formed of a superelastic material, stainless steel wire, Nitinol, cobalt-chromium-nickel-molybdenum-iron alloy, or cobalt chrome-alloy or any other suitable superelastic material that will result in a self-opening or self-expanding filter. In this embodiment, the filter struts 12 are preferably formed from wire having a round cross-section with a diameter of at least about 0.015 inches. Of course, it is not necessary that the struts 12 have a round or near round cross-section. For example, the struts 12 could take on any shape with rounded edges to maintain non-turbulent blood flow therethrough. In another form, the struts 12 could have non-rounded edges.

The filter struts 12 may be formed from any suitable material that will result in a self-opening or self-expanding filter 10, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the transition temperature is chosen to be slightly below normal body temperature of humans, which is about 98.6° F. Thus, when the filter 10 is deployed in the vena cave 52 and exposed to normal body temperature, the alloy of the struts 12 will transform to austenite, that is, the remembered state, which for the present invention is an expanded configuration when the filter 10 is deployed in the blood vessel. To remove the filter 10, the filter 10 is cooled to transform the material to martensite which is more ductile than austenite, making the struts 12 more malleable. As such, the filter 10 can be more easily collapsed and pulled into the sheath for removal.

In other embodiments, the filter struts 12 are made from Nitinol with a transition temperature that is above normal body temperature of humans, which is about 98.6° F. Thus, when the filter 10 is deployed in the vena cava and exposed to normal body temperature, the struts 12 are in the martensitic state so that the struts are sufficiently ductile to bend or form into a desired shape, which for the present invention is an expanded configuration. To remove the filter, the filter is heated to transform the alloy to austenite so that the filter becomes rigid and returns to a remembered state, which for the filter 10 is a collapsed configuration.

Notably, other materials allowing for a delivery and removal of the filter 10 by elastic deformation are well within the scope of the present invention.

The above description relating to the filter device 10 is exemplary. It will be appreciated that the retrieval system 60 or 160 described herein can be used with a variety of other filter designs that are dimensioned and configured to be deployed in the vena cava, or other body vessel, and further configured to be manually retrieved from the vena cava or other body vessel using a retrieval device.

Figure 3:
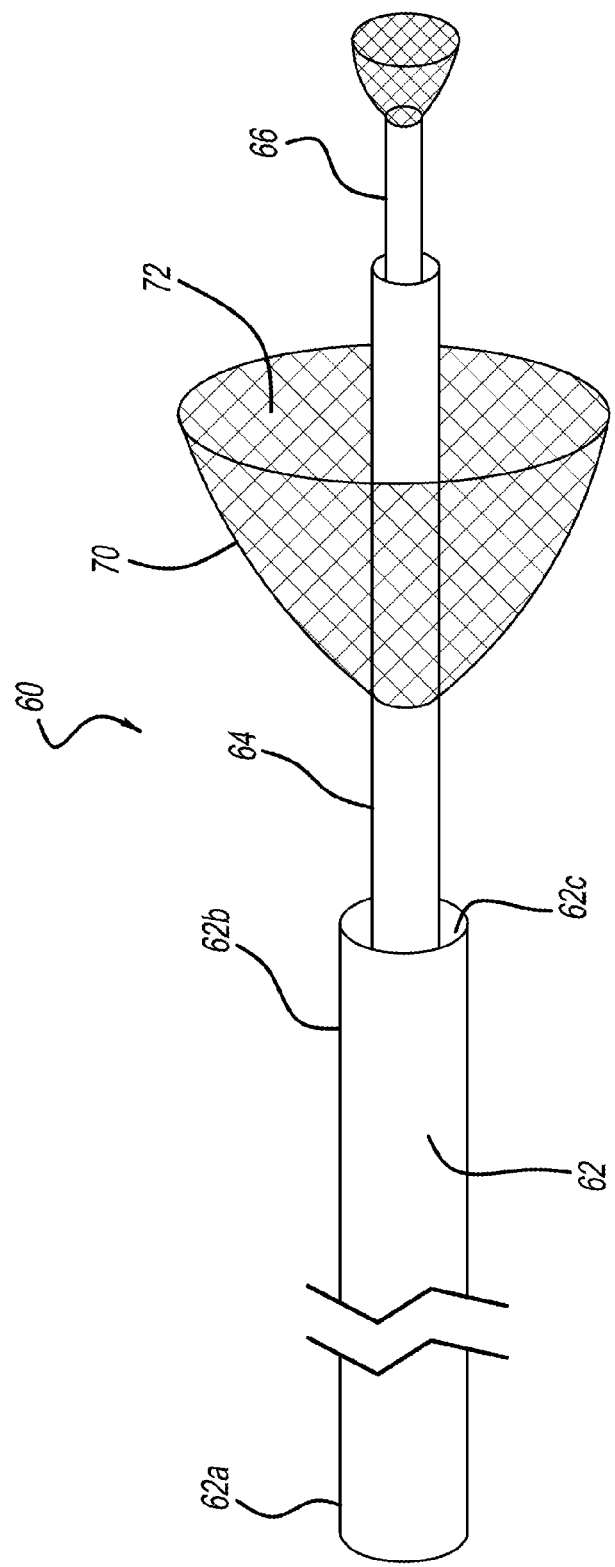
FIG. 3 illustrates a schematic view of a system for retrieving the filter.

As shown in FIG. 3, the system 60 includes three main components that operate together to retrieve the filter 10 from the body. The system 60 includes an access sheath 62, an intermediate tube or clot catch 64, and a retrieval device or filter catch 66. Each of these components can have an elongate shape and define longitudinal axes thereof between their proximal and distal ends.

The access sheath 62, shown in FIG. 4, includes proximal and distal ends 62a, 62b with corresponding openings and defines a lumen 62c extending from the proximal end 62a to the distal end 62b and defining a longitudinal axis therebetween. The access sheath 62 can have a size of approximately 12 French, in a preferred form, or could be smaller. The access sheath 62 may have a wall thickness depending on the material used or, for example, about 0.010 to 0.025 inches. Of course, other sizes could also be used to suit the needs of the user.

The clot catch 64, shown in FIG. 5, is configured to be received within the access sheath 62 and to be moveable relative to the access sheath 62 in the longitudinal direction. The clot catch 64 includes proximal and distal ends 64a, 64b with corresponding openings and defines a lumen 64c extending from the proximal end to the distal end and defining a longitudinal axis therebetween. The clot catch 64, being moveable relative to the access sheath 62, can be extended out of the distal end 62b of the access sheath 62.

The system 60 also includes a first mesh 70 that is configured to catch clots or other embolic material that may become loose during retrieval of the filter 10. The first mesh 70 is coupled to an outer surface of the clot catch 64, preferably relatively near the distal end 64b of the clot catch. The mesh 70 extends circumferentially around the clot catch 64 and extends radially away from the outer surface thereof. The mesh 70 defines a generally concave shape facing distally that defines a cavity 72 therein. The distal facing cavity 72 is directed toward the filter 10 during retrieval, such that the mesh 70 can catch embolic material that becomes dislodged during retrieval.

The mesh 70 can be made from a variety of known mesh materials that have a mesh size configured to allow for blood to flow therethrough while preventing emboli from passing.

The mesh 70 is configured to be collapsible such that it can be disposed within the access sheath lumen 62c between the clot catch 64 and the access sheath 62 during delivery of the system toward the filter 10. The mesh 70 is preferably self-expandable such that after being exposed from the distal end 62b of the sheath 62, the mesh 70 will radially expand into engagement with the vessel wall at the location of the deployment. This expansion into engagement with the vessel wall will thus result in emboli travelling toward the clot catch to be retained within the mesh 70 and on the outside of the clot catch 64.

The filter catch 66, shown in FIG. 6A-6C is configured to be disposed within the lumen 64c of the clot catch 64 and to be longitudinally moveable relative to the clot catch 64 and the access sheath 62. The filter catch 66 includes proximal and distal ends 66a, 66b and defines a longitudinal axis therebetween. The filter catch 66 has a generally elongate shape, having a thickness that ensures a combination of flexibility such that it can be routed through tortuous body vessels as well as pushability such that it can be fed distally away from a user without substantial kinking or undesired bending.

The filter catch 66 can include a main body portion or shaft 66c that is made of a solid wire or coiled wire having an overall major diameter of about 0.015 to 0.060 inches, in a preferred form. Other body types known in the art having desirable pushability and flexibility can also be used.

The system also includes a retrieval member 74 coupled to the distal end 66b of the filter catch 66. In one form, shown in FIG. 6A, the retrieval member 74 can be in the form of a second mesh 76. The second mesh 76 can be made from the same material as the first mesh 70, and can be similarly radially self-expanding. However, it will be appreciated that the second mesh 76 could be made from a different material and/or not self-expanding.

The mesh 74 is preferably collapsible such that it can be disposed within the clot catch lumen 64c when the filter catch 66 is likewise disposed therein during delivery of the system 60. With a self-expandable mesh 76, the mesh 76 will expand after being exposed from the clot catch 64 and advanced toward the filter 10 to retrieve the filter 10 from the vessel.

In another form, shown in FIG. 6B, the retrieval member 74 can be in the form of a plurality of loops 78. Each of the loops 78 can have first and second ends that are coupled to the distal end 66b of the filter catch 66. Alternatively, the loops 78 can be in the form of a closed loop knotted at the end of the material of the loop to define an eyelet.

In yet another form, shown in FIG. 6C, the retrieval member 74 can be in the form of a "bird's-nest" type structure with a wire or flexible member that bends and twists in a random and tortuous manner to define a plush head 80. This can be formed by a single flexible member or multiple flexible members to create the bird's nest.

In each of the above embodiments of the retrieval member 74, the member 74 is configured to cooperate with the hook 22 of the filter 10 such that contact between the hook 22 and the member 74 will result in a coupling between the two that will resist inadvertent decoupling.

For example, by contacting the hook 22 with the mesh 76, the hook 22 will become coupled within the perforations of the mesh 76, such that pulling on the mesh 76 will pull on the hook 22, or applying a distal force on the filter 10 will result in the hook 22 puling on the mesh 76, but the filter will be limited from distal translation by the mesh 76. Similarly, the loops 78 will cause the hook 22 to be coupled through one or more of the loops 78, resulting in the same relative force transmission. Likewise, the hook 22 will become entangled in the plush head 80 formed by the bird's nest.

Thus, by coupling the filter 10 to the filter catch 66 via the retrieval member 74, the filter 10 can be retrieved by the filter catch 66, and emboli that result from retrieving the filter 10 will be captured by the mesh 70 of the clot catch 64.

The above system 60 has been described as having three major components: the access sheath 62, the clot catch 64, and the filter catch 66. In another embodiment, a system 160 can include a fourth major component in the form of an inner sheath 90.

Figure 7:
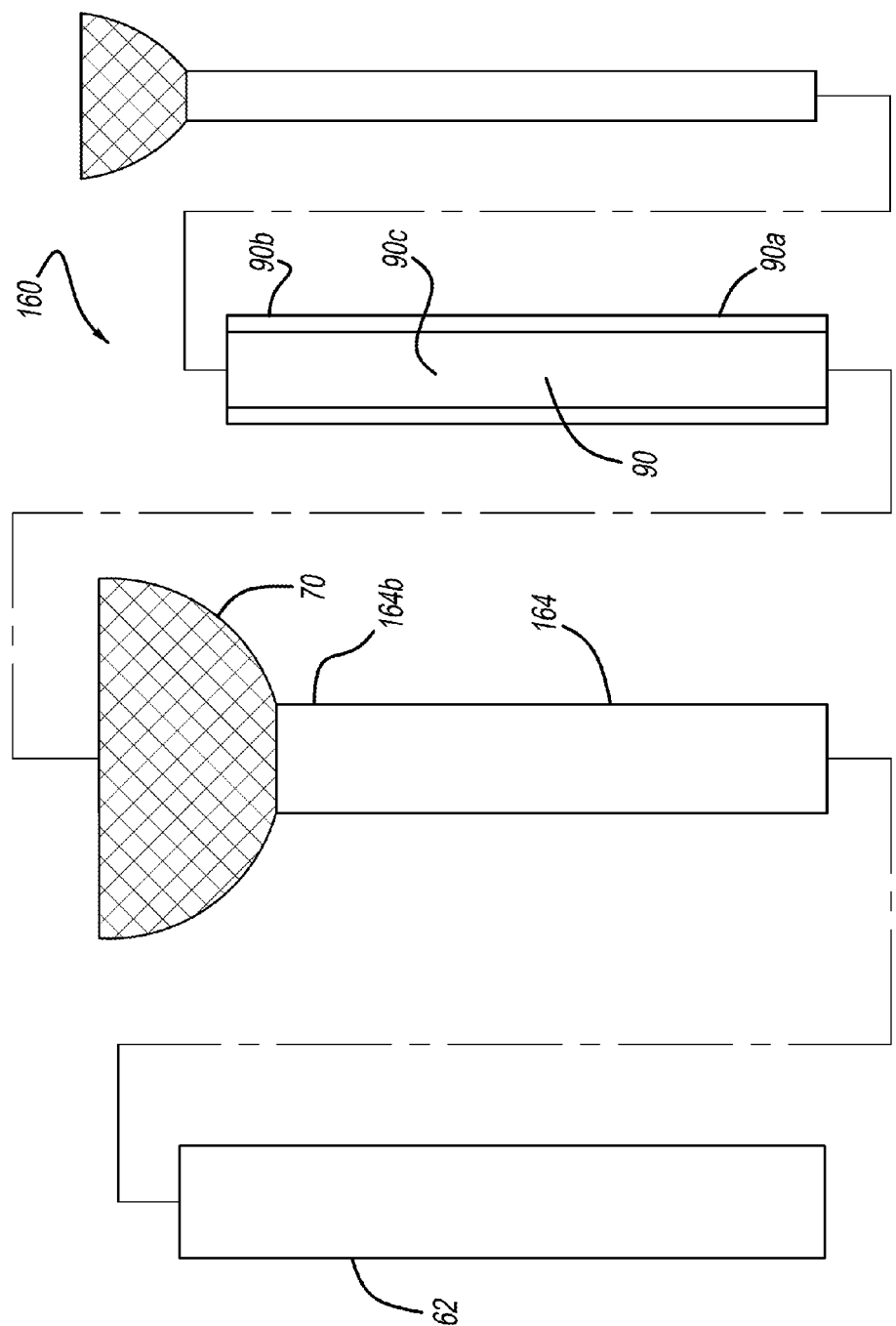
FIG. 7 illustrates an alternative retrieval system having an inner sheath.

With reference to FIG. 7, the system 160 can include the inner sheath 90 that can be have a similar configuration to the access sheath 62, wherein the inner sheath 90 includes proximal and distal ends 90a, 90b with corresponding openings and a lumen 90c extending therebetween and defining a longitudinal axis. The inner sheath 90 is sized and configured to be disposed within the lumen of an alternative clot catch 164, which is similar to the clot catch 64, but with the mesh 70 extending from a distal end 164b with the filter catch 66 being disposed within the lumen of the inner sheath 90 in the delivery configuration. The inner sheath 90 is also moveable longitudinally relative to the access sheath 62, the clot catch 164, and the filter catch 66.

The inner sheath 90 extends distally out of the clot catch 164 and is used to capture the filter 10 after the filter catch 66 has been coupled thereto during retrieval. In this regard, the inner sheath 90 can be considered redundant relative to the portion of the clot catch 64 that extends distally beyond the mesh 70 in the three part system described previously. Thus, in the embodiment including the inner sheath 90, the mesh 70 is attached at the distal end 164b of the clot catch 164. In this approach, the mesh 70 can be attached either to the inside surface of the clot catch 164 within the lumen 64c, or to the outside surface of the clot catch 164. In the case where the mesh 70 attaches within the lumen 64c, the distal end 164b of the body portion of the clot catch 164 will be disposed proximally of the exposed portion of the mesh 70. In the case where the mesh 70 attaches to the outer surface of the clot catch 164, the distal end 164b of the body portion of the clot catch 64 can extend into the cavity defined by the mesh 70, or can extend beyond the end of the mesh 70, similar to the configuration of the clot catch 64 of the three-part system.

Thus, while the inner sheath 90 may be redundant to the portion of the clot catch 64 that extends distally beyond the attachment point of the mesh 70, the inner sheath 90 can still be used with embodiments of the clot catch 64 that include this distal extension, such as the embodiment shown in the three part system. However, in a preferred form, the four part system utilizing the inner sheath 90 does not include a portion of the clot catch 164 extending substantially beyond the attachment point of the mesh 70.

Both the three-part system 60 and the four-part system 160 can be used to retrieve the filter 10 that has been deployed within the body vessel. The three part system includes fewer components and therefore requires manipulation of fewer components. In the three-part system, the clot catch 64 is typically translated distally to capture the filter 10 therein. The four-part system includes an additional component in the form of the inner sheath 90, but does not typically include translation of the clot catch 64 to capture the filter 10, as this is typically performed by the inner sheath 90. However, it will be appreciated that in both systems, the clot catch 64 can be translated distally to capture the filter 10. Moreover, in some instances, translation of the clot catch 64 or inner sheath 90 may not be necessary or desired to capture the filter. In these cases, the filter 10 can be pulled directly into the clot catch 64 and/or the inner sheath 90 for retrieval.

The three-part system 60 includes a delivery configuration, where the filter catch 66 and retrieval member 74 are housed within the lumen 64c of the clot catch 64, and the clot catch 64 and mesh 70 are housed within the lumen 62c of the access sheath 62. The retrieval member 74 is disposed proximally of the distal end 64b of the clot catch 64. The distal end 64b of the clot catch 64 is disposed proximally of the distal end of the access the sheath 62.

The three-part system 60 includes a retrieval configuration, where the retrieval member 74 is disposed distally from the distal end 64b of the clot catch 64, and the mesh 70 and distal end 64b of the clot catch 64 is disposed distally of the distal end 62b of the access sheath 62. The mesh 70 is expanded radially larger than the access sheath 62 and the filter catch 66.

The four-part system 160 includes a delivery configuration, where the filter catch 66 and retrieval member 74 are housed within the lumen 90c of the inner sheath 90. The inner sheath 90 is housed at least partially within the lumen 164c of the clot catch 164, and the clot catch 164 and mesh 70 are housed within the lumen 62c of the access sheath 62. The retrieval member 74 is disposed proximally of the distal end 62b of the access sheath 62 and the distal end 90b of the inner sheath 90, and optionally disposed proximally of the distal end 164b of the clot catch 164. The distal end 164b and the mesh 70 of the clot catch 164 is disposed proximally of the distal end of the access the sheath 62.

The four-part system 160 includes a retrieval configuration, where the retrieval member 74 is disposed distally from the distal end 164b of the clot catch 164 and distally from the mesh 70, and the mesh 70 and distal end 164b of the clot catch 64 are disposed distally of the distal end 62b of the access sheath 62. The mesh 70 is expanded radially larger than the access sheath 62 and the filter catch 66. The distal end 90b of the inner sheath 90 is disposed distally from the distal end 164b of the clot catch 164 and proximally of the retrieval member 74.

Having described the components of the various embodiments of the system 60, 160, the use of the system 60, 160 to retrieve the filter 10 from the vena cava or other body vessel will now be described.

With reference to FIG. 8, to retrieve the filter 10, the system 60 is delivered to the location of the filter 10 in the delivery state. Once at the retrieval location, the system 60 can be converted to the retrieval configuration.

The clot catch 64 can be exposed from the access sheath 62 such that the mesh 70 is exposed and allowed to radially expand across the body vessel to into engagement with the vessel wall. The retrieval member 74 of the filter catch 66 can be exposed from the clot catch 64, either by retracting the clot catch 64 relative to the mesh 76 or by advancing the mesh 76 relative to the clot catch 64. It will be appreciated that any reference to exposing the mesh 76 can include one or both of these methods. With the mesh 76 exposed, the mesh 76 can be advanced into engagement with the hook member 22 of the filter 10, thereby coupling the filter 10 to the retrieval device 60.

With reference to FIG. 9, the clot catch 64 can then be translated toward the filter 10, where the filter 10 will be enveloped by the distal end 64b of the clot catch 64. The struts 12 will compress radially inward to fit within the lumen 64c of the clot catch 64. When the clot catch 64 contacts the filter 10, the mesh 76 and its engagement with the hook 22 will prevent the filter 10 from being pushed away and will allow the clot catch 64 to receive the filter 10. FIG. 9 illustrates the clot catch 64 translated distally to capture the filter 10.

FIGS. 8 and 9 also illustrate various emboli E being captured by the mesh 70 of the clot catch 70 during retrieval.

Figure 10:
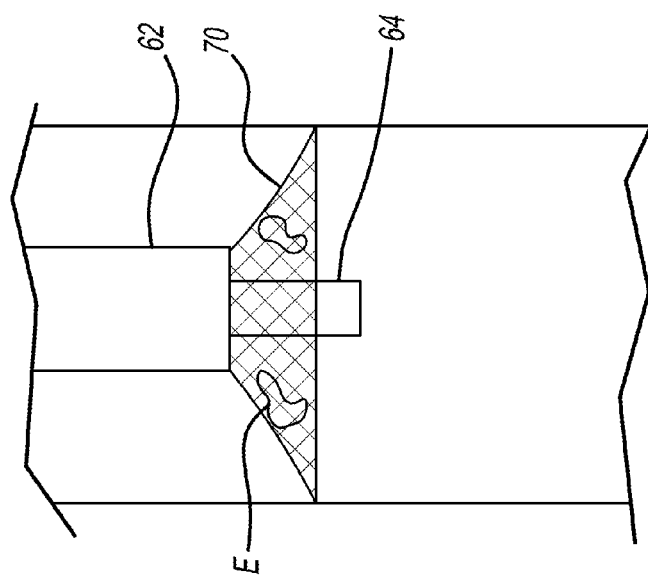

With reference to FIG. 10, once the filter 10 has been sufficiently captured by the clot catch 64, the access sheath 64 can be advanced distally to capture the mesh 70, with the mesh 70 of the clot catch 64 being partially captured by the sheath 62. In this figure, the filter 10 has been completely enveloped by the clot catch 64. However, it will be appreciated that the sheath 62 can be advanced to capture the mesh 70 and the filter 10 can be retrieved without having been fully enveloped by the clot catch 64, if desired. Further translation of the sheath 62 will fully capture the clot catch 64 and the mesh 70, and the system 60, with the filter 10 captured therein, can be withdrawn from the patient's body.

The above described method relating to the three part system 60 has been described with reference to the clot catch 64 and sheath 62 being advanced distally to capture the filter 10 and clot catch 64, respectively. It will be appreciated that this three-part system 60 can also be used by retracting components, if desired.

For example, instead of translating the clot catch 64 distally to capture the filter 10, with the filter 10 limited from distal translation by the retrieval member 74, the filter catch 66 can instead be retracted proximally into the clot catch 64, with the clot catch 64 held stationary. Alternatively, a combination of distal translation of the clot catch 64 and proximal retraction of the filter catch 66 can be used. If retracting the filter catch 66 to perform this retrieval, the filter 10 will have preferably been disengaged from the vessel wall prior to retracting the filter catch 66 and filter 10 to avoid instances of the filter 10 scraping the vessel wall as it is retracted. To limit instances of the filter 10 potentially scraping the vessel wall, the filter 10 is preferably retrieved by translating the clot catch 64 distally to capture the filter 10, while holding the filter catch 66 generally in place. In either approach, emboli that may come loose during retrieval of the filter 10 will be captured by the mesh 70.

Similarly, the clot catch 64 and filter catch 66 can be retracted into the sheath 62 instead of advancing the sheath 62. Or, a combination of retraction of the clot catch 64 and filter catch 62 with distal translation of the sheath 62 can also be used.

These various combination of retractions and distal translations of the components of the three-part system 60 will be understood by skilled artisans. In any of the combinations, the filter 10 is preferably captured prior to capturing the mesh 70 in order to limit emboli from flowing past the mesh 70. Once the filter 10 has been detached from the vessel wall, the risk of emboli being released is reduced.

The four-part system 160 operates similarly to the three-part system, but includes the translation and/or retraction of the inner sheath 90.

Figure 11:
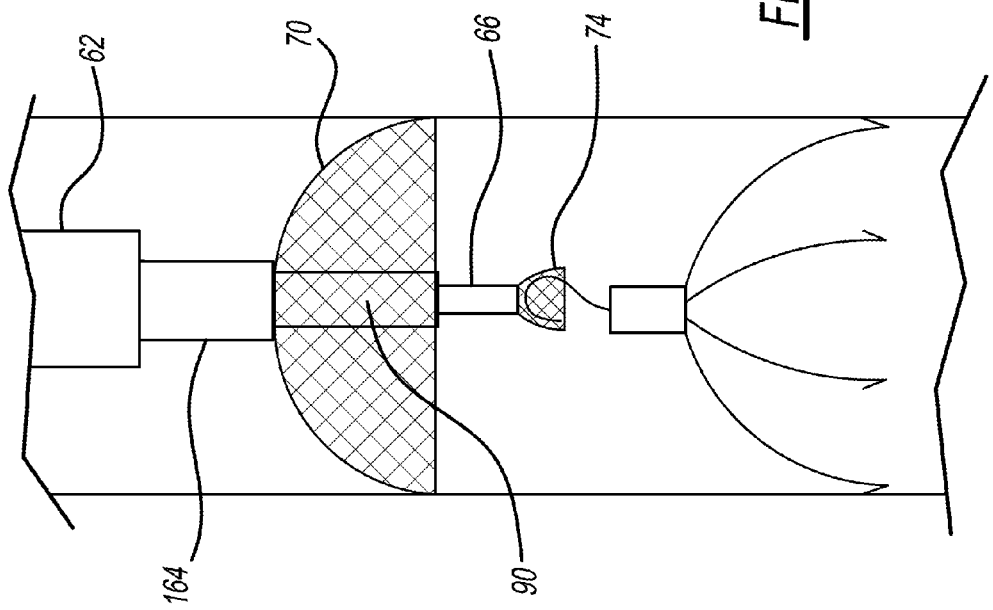
FIGS. 11-14 illustrates a method for retrieving the filter using the system of FIG. 7.

With reference to FIG. 11, the clot catch 164 and mesh 70 are exposed from the access sheath 62. The clot catch 164 is moved distally relative to the sheath 62 by either distal translation, proximal retraction of the sheath 62, or a combination of both.

Once the mesh 70 is exposed and has expanded into engagement with the vessel wall, the filter catch 66 with retrieval member 74 is exposed from the clot catch 164 and into engagement with the hook 22 of the filter 10.

The inner sheath 90 is shown in FIG. 11 exposed from the clot catch 164. The inner sheath can be exposed from the clot catch 164 prior to exposing the filter catch 66 or after exposing the filter catch 66 from the clot catch 164.

Figure 12:
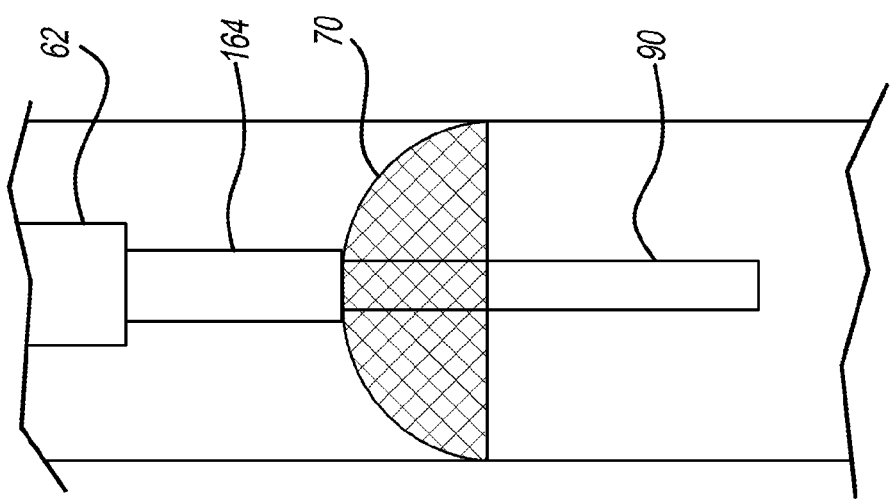

With reference to FIG. 12, once the filter catch 66 is engaged with the filter 10, the filter 10 can be retrieved into the inner sheath 90. This can be performed by translating the inner sheath 90 distally, retracting the filter catch 66 proximally, or a combination of both. If retracting the filter catch 66 to perform this retrieval, the filter 10 will have preferably been disengaged from the vessel wall prior to retracting the filter catch 66 and filter 10 to avoid instances of the filter 10 scraping the vessel wall as it is retracted. To limit instances of the filter 10 potentially scraping the vessel wall, the filter 10 is preferably retrieved by translating the inner sheath 90 distally to capture the filter 10, while holding the filter catch 66 generally in place. During retrieval, the clot catch 164 is preferably prevented from being captured by the access sheath 62 so that emboli that may break loose during filter retrieval are captured in the mesh 70.

Figure 13:
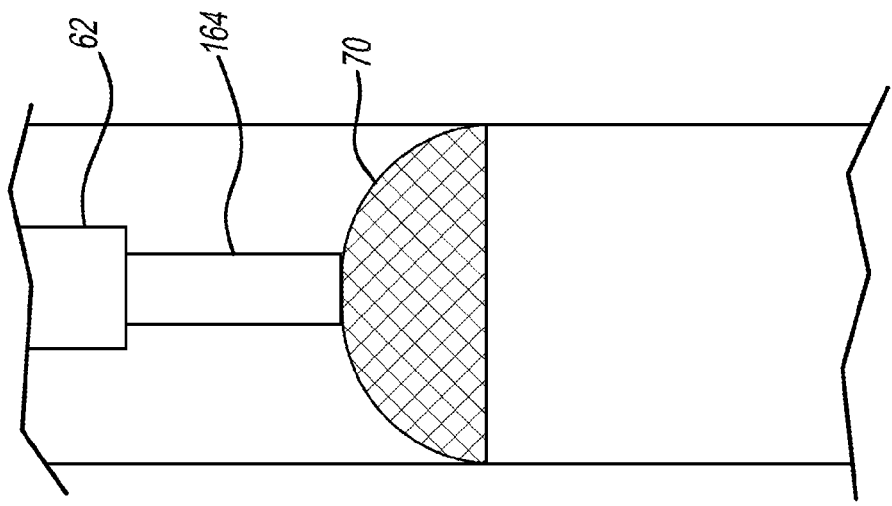

With reference to FIG. 13, once the filter 10 has been removed from the vessel wall and at least partially retrieved by the inner sheath 90, the access sheath 90, with the filter 10 captured therein, can be captured by the clot catch 164. This can be done by retracting the access sheath 90 and the filter catch 66 proximally, distally translating the clot catch 164, or a combination of both.

Figure 14:
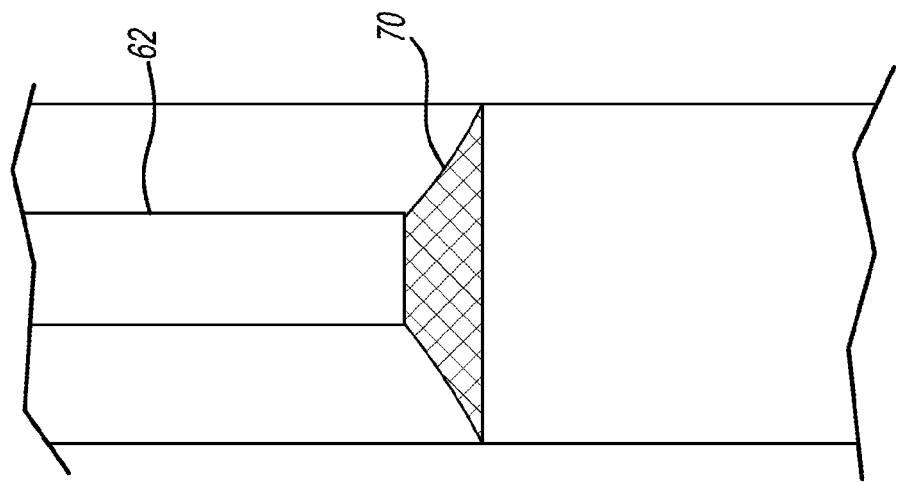

With reference to FIG. 14, once the inner sheath 90, filter catch 66, and filter 10 have been captured by the clot catch 164, the clot catch 164 can be captured by the access sheath 64 in the same manner as the three-part system described above.

In an alternative approach, the clot catch 164 can be captured by the access sheath 62 prior to the inner sheath 90 being captured by the clot catch 164. In this approach, the inner sheath 90 can remain exposed from the end of the access sheath 62. In this approach, the system can be retracted from the patient's body with the inner sheath 90 remaining extended from the access sheath 62, or the inner sheath 90 can be captured by the access sheath 62 prior to retracting the system from the patient.

It will be appreciated that the various components of the four-part system 160 can be translated relative to each other in various combinations of distal translation and proximal retraction, depending on the needs of the user.

In both the three-part system 60 and the four-part system 160, it is preferable that the mesh 70 attached to the clot catch 64 or 164 is exposed and spans the body vessel prior to engaging the filter 10 with the filter catch 66 to limit occurrences of emboli travelling distally past the mesh 70 during retrieval.

The four-part system 160 is preferably used when the user desires that the mesh 70, clot catch 164, and filter catch 66 remain longitudinally stationary during retrieval of the filter 10. The inner sheath 90 can be the only component translated in this approach until the filter 10 has been sufficiently captured. This approach limits translation of the clot catch 164 and potential movement of the mesh 70 that captures emboli during retrieval.

The three-part system 60 requires translation of either the filter catch 66 or the clot catch 164. In some cases, the clot catch 164 will translate distally to capture the filter 10, which is held longitudinally stationary in order to separate the struts 12 of the filter 10 from the vessel wall. However, if the filter struts 12 are released from the vessel wall through other known methods, the filter catch 66 can be retracted with the clot catch 164 held stationary.

The above described systems 60, 160 and method can be used for a variety of filter types and is not limited to strut-type filters. Moreover, the systems and methods described herein can be used for retrieval of other implantable medical devices.

While the present invention has been described in terms of preferred embodiments, it will be understood, of course, that the invention is not limited thereto since modifications may be made to those skilled in the art, particularly in light of the foregoing teachings.

What is claimed is:

1. A system for retrieving a medical device from within a body lumen, the system comprising:
   - an access sheath having proximal and distal ends, corresponding proximal and distal openings, and a lumen extending therebetween and defining a longitudinal axis;
   - an intermediate tube having proximal and distal ends, corresponding proximal and distal openings, and a lumen extending therebetween, wherein the intermediate tube is disposed at least partially within the access sheath lumen and movable longitudinally relative to the access sheath;
   - a first mesh member attached to the intermediate tube and being biased radially outward to define a concave shape with a concavity facing the distal direction; and
   - a retrieval device having an elongate shape and having proximal and distal ends, and a retrieval member coupled thereto, wherein the retrieval device is disposed at least partially within the lumen of the intermediate tube and moveable longitudinally relative to the intermediate tube;
   - wherein the system includes a delivery configuration with the retrieval member and the distal end of the intermediate tube being disposed proximally of the distal opening of the access sheath; and
   - wherein the system includes a retrieval configuration with the retrieval member disposed distally of the distal opening of the intermediate tube, the first mesh member disposed distally of the distal opening of the access sheath and expanded radially outward to define the concave shape;
   - wherein the first mesh member is attached to the intermediate tube at a location proximal from the distal opening of the intermediate tube, and the first mesh member is a distal most mesh member attached to the intermediate tube.

2. The system of claim 1, wherein the retrieval member comprises a second mesh member.

3. The system of claim 1, wherein the distal opening of the intermediate tube is disposed distally from a distal end of the first mesh member.

4. The system of claim 1, wherein the distal opening of the intermediate tube is disposed proximally from a distal end of the first mesh member and distally from a proximal end of the first mesh member.

5. The system of claim 1, wherein the retrieval member comprises a plurality of loops.

6. The system of claim 1, wherein the retrieval member comprises at least one flexible member having a random tortuous path defining a bird's nest.

7. A method for retrieving a medical device from a body vessel using the system of claim 1, the method comprising:
   delivering the system of claim 1 in the delivery configuration toward a medical device located within a body vessel,
      wherein the intermediate tube comprises a clot catch;
      wherein the first mesh member comprises an expandable mesh attached to the clot catch;
      wherein the retrieval device comprises a filter catch extending the clot catch distally from the access sheath;
   exposing the expandable mesh from the access sheath;
   expanding the expandable mesh into engagement with a wall of the body vessel;
   extending the filter catch and retrieval member distally from the clot catch;
   capturing a portion of a medical device with the retrieval member;
   capturing at least a portion of the medical device within the clot catch;
   capturing the clot catch and the expandable mesh within the access sheath;
   retracting the system proximally.

8. The method of claim 7, wherein the system further comprises an inner sheath disposed within the clot catch and the access sheath.

9. The method of claim 8 further comprising extending the inner sheath distally from the clot catch.

10. The method of claim 9 further comprising capturing the medical device at least partially within the inner sheath.

11. The method of claim 10 further comprising capturing the inner sheath and medical device within the access sheath.

12. The method of claim 11, wherein the clot catch is held longitudinally stationary during capture of the inner sheath and medical device within the access sheath.

13. The method of claim 10, wherein the clot catch is held longitudinally stationary during capture of the medical device within the inner sheath.

14. The method of claim 7, wherein the filter catch is held longitudinally stationary during capture of the filter catch by the clot catch.

15. The method of claim 7, wherein the clot catch is held longitudinally stationary during capture of the clot catch by the access sheath.

16. The method of claim 7 further comprising capturing emboli within the expandable mesh during capture of the medical device.

17. A system for retrieving a medical device from within a body lumen, the system comprising:
   an access sheath having proximal and distal ends, corresponding proximal and distal openings, and a lumen extending therebetween and defining a longitudinal axis;
   an intermediate tube having proximal and distal ends, corresponding proximal and distal openings, and a lumen extending therebetween, wherein the intermediate tube is disposed at least partially within the access sheath lumen and movable longitudinally relative to the access sheath;
   a first mesh member coupled to the intermediate tube and being biased radially outward to define a concave shape with a concavity facing the distal direction, wherein the first mesh member has a proximal end that is fixed to an exterior surface of the intermediate tube, and a distal end is radially expandable away from the exterior surface of the intermediate tube, wherein the first mesh member defines a plurality of openings such that blood will flow through the first mesh member; and
   a retrieval device having an elongate shape and having proximal and distal ends, and a retrieval member coupled thereto, wherein the retrieval device is disposed at least partially within the lumen of the intermediate tube and moveable longitudinally relative to the intermediate tube;
   wherein the system includes a delivery configuration with the retrieval member and the distal end of the intermediate tube being disposed proximally of the distal opening of the access sheath; and
   wherein the system includes a retrieval configuration with the retrieval member disposed distally of the distal opening of the intermediate tube, the first mesh member disposed distally of the distal opening of the access sheath and expanded radially outward to define the concave shape
   further comprising an inner sheath having proximal and distal ends, corresponding proximal and distal openings, and a lumen extending therebetween, wherein the inner sheath is disposed within the intermediate tube, and the retrieval device is disposed within the inner sheath
   wherein the distal opening of the inner sheath is disposed distally of a distal end of the first mesh member in the retrieval configuration
   wherein the retrieval configuration includes a first retrieval state and a second retrieval state, and the retrieval member is disposed distally of the distal opening of the inner sheath in the first retrieval state and disposed entirely proximally of the distal opening of the inner sheath in the second retrieval state.

* * * * *